United States Patent [19]
MacLeod et al.

[11] Patent Number: 5,663,352
[45] Date of Patent: Sep. 2, 1997

[54] 4-PHENYL-4-PHENYLPROPYL(ENYL)-PIPERIDINES AS TACHYKININ ANTAGONISTS

[75] Inventors: Angus Murray MacLeod, Bishops Stortford; Kevin John Merchant, Stevenage; Graeme Irvine Stevenson, Saffon Walden, all of United Kingdom

[73] Assignee: Merck Sharp & Dohme Limited, Harlow, England

[21] Appl. No.: 583,014

[22] PCT Filed: Jul. 21, 1994

[86] PCT No.: PCT/GB94/01576

§ 371 Date: Jan. 19, 1996

§ 102(e) Date: Jan. 19, 1996

[87] PCT Pub. No.: WO95/04042

PCT Pub. Date: Feb. 9, 1995

[30] Foreign Application Priority Data

Jul. 30, 1993 [GB] United Kingdom ............... 9315808

[51] Int. Cl.⁶ .................. C07D 211/14; C07D 211/12; A61K 31/445
[52] U.S. Cl. .................. 546/240; 546/210; 546/230; 546/234; 546/239
[58] Field of Search .................. 546/240, 239, 546/234, 230, 210

[56] References Cited

U.S. PATENT DOCUMENTS 5,462,947  10/1995  Svensson et al. ............. 514/317

FOREIGN PATENT DOCUMENTS

| 0 528 495 | 2/1993 | European Pat. Off. . | |
|---|---|---|---|
| 2678269 | 6/1991 | France | 546/240 |
| WO94/10165 | 5/1994 | WIPO . | |
| WO94/13639 | 6/1994 | WIPO . | |

OTHER PUBLICATIONS

Maggi, C.A. et al.: J. Auton. Pharmacal (1993) vol. 13, pp. 60–66.

*Primary Examiner*—C. Warren Ivy
*Assistant Examiner*—C. S. Aulakh
*Attorney, Agent, or Firm*—J. Eric Thies; David L. Rose

[57] ABSTRACT

The present invention relates to compounds of formula (I), and pharmaceutically acceptable salts and prodrugs thereof, wherein X represents a propylene or propenylene chain optionally substituted by one or more of $R^4$, $R^5$, $R^6$ and $R^7$; m is 2, 3 or 4; n is 0, 1 or 2 when m is 2 or 3, and n is 0 or 1 when m is 4; $R^1$ represents optionally substituted phenyl; $R^2$ represents optionally substituted phenyl, heteroaryl, benzhydryl or benzyl; $R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, CONHphenyl($C_{1-4}$alkyl), $COCO_2R^{10}$, $COCONR^{10}R^{11}$, $SO_2R^{15}$, $CONR^{10}SO_2R^{15}$ and optionally substituted phenyl), $Y$—$R^8$ or $CO$—$Z$—$(CH_2)_q$—$R^{12}$; $R^4$ and $R^5$ each independently represent H, $C_{1-6}$alkyl, $C_{3-6}$cycloalkyl, $C_{3-5}$cycloalkylmethyl, hydroxy or $C_{1-6}$alkoxy, or $R^4$ and $R^5$ together form a group =O; $R^6$ and $R^7$ each independent represents H, $C_{1-6}$alkyl, $C_{3-6}$cycloalkyl, $C_{3-5}$cycloalkylmethyl, hydroxy or $C_{1-6}$alkoxy or $R^6$ and $R^7$ together form a group =O; $R^8$ represents an optionally substituted aromatic heterocycle; $R^9$ represents H, $C_{1-6}$alkyl, $C_{3-6}$cycloalkyl, $C_{3-5}$cycloalkylmethyl, or phenyl; $R^{10}$ and $R^{11}$ each independently represent H, $C_{1-6}$alkyl, $C_{3-6}$cycloalkyl or $C_{3-5}$cycloalkylmethyl; $R^{12}$ represents $NR^{13}R^{14}$ or an optionally substituted aromatic or non-aromatic azacyclic or azabicyclic group; $R^{13}$ and $R^{14}$ each independently represent H, $C_{1-6}$alkyl, $C_{3-6}$cycloalkyl, $C_{3-5}$cycloalkylmethyl, optionally substituted phenyl or phenyl$C_{1-4}$alkyl; $R^{15}$ represents $C_{1-6}$alkyl, $C_{3-6}$cycloalkyl, $C_{3-5}$cycloalkylmethyl, trifluoromethyl or optionally substituted phenyl; Y represents a hydrocarbon chain of 1, 2, 3 or 4 carbon atoms which may optionally be substituted by oxo; Z represents $CH_2$, O, S or $NR^{10}$; and q represents 0, 1, 2, 3, 4, 5 or 6. The compounds are tachykinin antagonists useful for treating pain or inflammation, migraine or emesis.

19 Claims, No Drawings

4-PHENYL-4-PHENYLPROPYL(ENYL)-PIPERIDINES AS TACHYKININ ANTAGONISTS

This invention relates to a class of azacyclic compounds, which are useful as tachykinin antagonists. More particularly, the compounds of the invention comprise an azacyclic ring system substituted by an aryl moiety and an arylalkyl or arylalkenyl moiety.

The tachykinins are a group of naturally-occurring peptides found widely distributed throughout mammalian tissues, both within the central nervous system and in the peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, Peptides (1985) 6 (suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists may also be useful in the treatment of emesis [F. D. Tattersall et. al., Eur. Pharmacol., (1993) 250, R5–R6]. Tachykinin antagonists are also believed to be useful in allergic conditions [Hamelet et al Can. J. Pharmacol. Physiol. (1988) 66 1361–7], immunoregulation [Lotz et al Science (1988) 2.41 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent specification no. 0 436 334), conjuctivitis, vernal conjunctivitis, contact dermatitis, atropic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of formula (I), or a pharmaceutically acceptable salt or prodrug thereof:

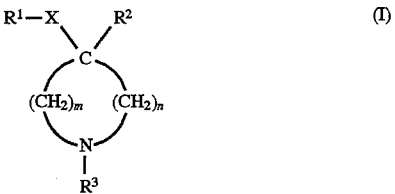

wherein

X represents a propylene or propenylene chain optionally substituted by one or more of $R^4$, $R^5$, $R^6$ and $R^7$;

m is 2, 3 or 4;

n is 0, 1 or 2 when m is 2 or 3, and n is 0 or 1 when m is 4;

$R^1$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, $-OR^a$, $-SR^a$, $-SOR^a$, $-SO_2R^a$, $-NR^aR^b$, $-NR^aCOR^b$, $-NR^aCO_2R^b$, $-CO_2R^a$ or $-CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, $-OR^a$, $-SR^a$, $-SOR^a$, $-SO_2R^a$, $-NR^aR^b$, $-NR^aCOR^b$, $-NR^aCO_2R^b$, $-CO_2R^a$ or $-CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONH$phenyl($C_{1-4}$alkyl), $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), $Y$—$R^8$ or $CO$—$Z$—$(CH_2)_q$—$R^{12}$;

$R^4$ and $R^5$ each independently represents H, $C_{1-6}$alkyl, $C_{3-6}$cycloalkyl, $C_{3-5}$cycloalkylmethyl, hydroxy or $C_{1-6}$alkoxy, or $R^4$ and $R^5$ together form a group =O;

$R^6$ and $R^7$ each independently represents H, $C_{1-6}$alkyl, $C_{3-6}$cycloalkyl, $C_{3-5}$cycloalkylmethyl, hydroxy or $C_{1-6}$alkoxy or $R^6$ and $R^7$ together form a group =O;

$R^8$ represents an optionally substituted aromatic heterocycle;

$R^9$ represents H, $C_{1-6}$alkyl, $C_{3-6}$cycloalkyl, $C_{3-5}$cycloalkylmethyl, or phenyl;

$R^{10}$ and $R^{11}$ each independently represent H, $C_{1-6}$alkyl, $C_{3-6}$cycloalkyl or $C_{3-5}$cycloalkylmethyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, $C_{3-6}$cycloalkyl, $C_{3-5}$cycloalkylmethyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, $C_{3-6}$cycloalkyl, $C_{3-5}$cycloalkylmethyl, trifluoromethyl or phenyl optionally substituted by one or more substituents selected from $C_{1-6}$alkyl, $C_{1-6}$alkoxy, halo and trifluoromethyl;

Y represents a hydrocarbon chain of 1, 2, 3 or 4 carbon atoms which may optionally be substituted by oxo;

Z represents $CH_2$, O, S or $NR^{10}$; and q represents 0, 1, 2, 3, 4, 5 or 6.

As used herein, the definition of each expression, when it occurs more than once in any structure, is intended to be independent of its definition elsewhere in the same structure.

The alkyl, alkenyl and alkynyl groups referred to with respect to the formulae herein may represent straight or branched groups. Thus, for example, suitable alkyl groups include methyl, ethyl, n- or iso-propyl and n-, sec-, iso- or tert-butyl. The cycloalkyl groups referred to above may be, for example, cyclopropyl, cyclobutyl, cyclopentyl or cyclohexyl. Similarly, suitable cycloalkylmethyl groups include cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs" ed. H. Bundgaard, Elsevier, 1985.

Those compounds according to the invention which contain one or more chiral centres may exist both as enantiomers and as diastereomers. It is to be understood that all such isomers and mixtures thereof are encompassed within the scope of the present invention.

Preferably m is 2.

When m is 2, n is preferably 2. When m is 3 or 4, n is preferably 0.

A preferred class of compounds of formula (I) is that wherein X represents a group $CR^4R^5CH_2CR^6R^7$, $CR^4=CHCR^6R^7$ or $CR^4R^5CH=CR^6$.

Suitably $R^4$ and $R^5$ each independently represents H, methyl, hydroxy or methoxy or $R^4$ and $R^5$ together represent =O.

Suitably $R^6$ and $R^7$ each independently represents H, methyl, hydroxy or methoxy or $R^6$ and $R^7$ together represent =O.

Suitable values for the group X include:

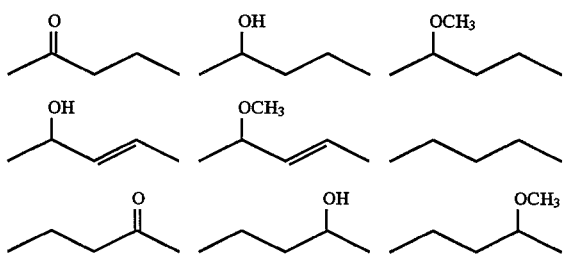

Preferably X represents $CR^4R^5CH_2CR^6R^7$ such as $CH_2CH_2CH_2$, $CH(OH)CH_2CH_2$ or $CH_2CH_2CH(OH)$. Preferably X represents $CH_2CH_2CH(OH)$.

Preferably $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy. Preferably $R^1$ represents phenyl substituted by one or more groups selected from $C_{1-6}$alkyl such as methyl and t-butyl, halo such as chloro, fluoro and bromo, and trifluoromethyl.

Preferably $R^1$ represents disubstituted phenyl, in particular 3,5-disubstituted phenyl, for example 3,5-disubstituted phenyl wherein the substituents are selected from $C_{1-6}$alkyl, halo and trifluoromethyl. More preferably $R^1$ represents 3,5-bis(trifluoromethyl) phenyl.

Suitable values for the group $R^2$ include unsubstituted or substituted phenyl, 5-membered heteroaryl such as thienyl, 6-membered heteroaryl such as pyridyl, and benzhydryl.

Preferably $R^2$ represents unsubstituted or substituted phenyl.

When $R^2$ represents substituted phenyl a preferred substituent is halo, especially fluoro.

When $R^8$ represents a substituted aromatic heterocycle, suitable substituents in the heterocyclic ring include one or more of $C_{1-6}$alkyl, $C_{3-6}$cycloalkyl, $C_{3-5}$cycloalkylmethyl, $C_{1-6}$alkoxy, phenyl, oxo, thioxo, halo, trifluoromethyl $NR^aR^b$ $NR^aCOR^b$, $CONR^aR^b$, $CO_2R^a$, $SR^a$, $SO_2R^a$ and $CH_2OR^a$, where $R^a$ and $R^b$ are as previously defined. Particular examples of suitable substituents include methyl, methoxy, phenyl, oxo, thioxo, bromo, iodo, $NH_2$, $SCH_3$, $CONH_2$ and cyano. Particularly preferred substituents include oxo and $NH_2$.

Suitable values for $R^8$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

Preferably $R^8$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably $R^8$ represents optionally substituted oxazolyl, oxadiazolyl, imidazolyl, thiadiazolyl, triazolyl, pyrazinyl, pyrimidinyl, pyridazinyl or triazinyl, or tetrazolyl substituted by $C_{1-6}$alkyl, preferably methyl.

It will be appreciated that, when the heterocyclic moiety $R^8$ is substituted by an oxo or thioxo substituent, different tautomeric forms are possible so that the substituent may be represented as =O or —OH, or =S or —SH, respectively. For the avoidance of doubt, all such tautomeric forms are embraced by the present invention.

When $R^{12}$ represents $NR^{13}R^{14}$, $R^{13}$ and $R^{14}$ are preferably both $C_{1-6}$alkyl such as methyl, ethyl, n-propyl, i-propyl, n-butyl, i-butyl or t-butyl. More preferably $R^{13}$ and $R^{14}$ will both represent methyl.

When $R^{12}$ represents an aromatic or non-aromatic azacycle or azabicycle it may contain one or more additional heteroatoms selected from O, S and N or groups $NR^{16}$, where $R^{16}$ is H, $C_{1-6}$alkyl or phenyl$C_{1-4}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^{12}$ represents an aromatic azacycle or azabicycle, suitable values of $R^{12}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^{12}$ represents a non-aromatic azacycle or azabicycle, suitable values of $R^{12}$ include morpholinyl, piperdinyl, pyrrolidinyl, piperazinyl, methylpiperazinyl, azanorbornanyl, azabicyclo[2.2.2]octanyl and azabicyclo [3.2.2]nonyl, preferably morpholinyl, methylpiperazinyl, quinuclidinyl (azabicyclo[2.2.2]octanyl) or azabicyclo [3.2.2]nonyl, more preferably quinuclidinyl.

Suitably Y represents a hydrocarbon chain of 1 or 2 carbon atoms optionally substituted by oxo, such as $CH_2$, C=O, $CH(CH_3)$, $CH_2(C=O)$ or $(C=O)CH_2$. Preferably Y represents $CH_2$, $CH(CH_3)$ or $CH_2(C=O)$, more preferably $CH_2$ or $CH(CH_3)$.

Suitably q represents 0, 1, 2 or 3.

Suitable values of $R^3$ include H, $COR^9$ such as $COCH_3$, $SO_2R^{15}$ such as $SO_2CH_3$, $C_{1-6}$alkyl such as $CH_3$, $CH(CH_3)_2$, $CH_2CH(CH_3)_2$ and $CH_2CH_2C(CH_3)_3$, $C_{1-6}$alkyl substituted by $CO_2R^{16}$ such as $CH_2CO_2CH_3$, $CH_2CO_2H$, $(CH_2)_3CO_2CH_3$ and $(CH_2)_3CO_2H$, $C_{1-6}$alkyl substituted by $CONR^{16}SO_2R^{15}$ such as $CH_2CONHSO_2CH_3$ and $CH_2CONHSO_2C_6H_5$, $C_{1-6}$alkyl substituted by phenyl, Y—$R^8$ and CO—Z—$(CH_2)_q$—$R^{12}$.

In one preferred subgroup of compounds according to the invention, $R^3$ represents H or $C_{1-6}$alkyl, more preferably H.

In a further preferred subgroup of compounds according to the invention $R^3$ represents Y—$R^8$.

A yet further preferred subgroup of compounds according to the invention is represented by compounds wherein $R^3$ is CO—Z—$(CH_2)_q$—$R^{12}$.

A particular sub-class of compounds according to the invention is represented by compounds of formula (Ia), and pharmaceutically acceptable salts and prodrugs thereof:

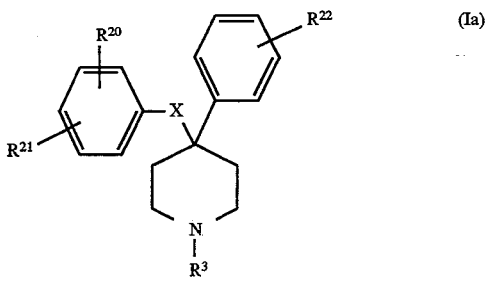

(Ia)

wherein $R^3$ and X are as defined for formula (I);

$R^{20}$ and $R^{21}$ independently represent H, $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl trimethylsilyl $OR^a$, $SR^a$ $SOR^a$, $SO_2R^a$, $NR^aR^b$, $NR^aCOR^b$, $NR^aCO_2R^b$, $CO_2R^a$ or $CONR^aR^b$, where $R^a$ and $R^b$ are as previously defined; and $R^{22}$ represents H or halo, preferably H or fluoro.

Particular values of $R^{20}$ and $R^{21}$ include H, chloro, bromo, methyl, t-butyl and trifluoromethyl. Preferably $R^{20}$ and $R^{21}$ are both other than H and are located at the 3- and 5-positions of the phenyl ring.

Specific compounds within the scope of the present invention include:

4-(3-(3',5'-bis(trifluoromethyl)phenyl)propionyl)-4-phenylpiperidine;

4-(3-(3',5'-bis(trifluoromethyl)phenyl)-1-hydroxy-3-propenyl)-4-phenylpiperidine;

4-(3-(3',5'-bis(trifluoromethyl)phenyl)-1-methoxy-3-propenyl)-4-phenylpiperidine;

4-(3-(3',5'-bis(trifluoromethyl)phenyl)-1-methoxypropyl)-4-phenylpiperidine;

4-(3-(3',5'-bis(trifluoromethyl)phenyl)-1-hydroxypropyl)-4-phenylpiperidine;

4-(3-(3',5'-bis(trifluoromethyl)phenyl)-3-ketopropyl)-4-phenylpiperidine;

4-(3-(3',5'-bis(trifluoromethyl)phenyl)-3-hydroxypropyl)-4-phenylpiperidine;

4-(3-(3',5'-bis(trifluoromethyl)phenyl)-3-methoxypropyl)-4-phenylpiperidine;

(R)-4-(3-(3',5'-bis(trifluoromethyl)phenyl)-3-hydroxypropyl)-4-phenylpiperidine;

(S)-4-(3-(3',5'-bis(trifluoromethyl)phenyl)-3-hydroxypropyl)-4-phenylpiperidine;

4-(3-(3',5'-bis(trifluoromethyl)phenyl)-3-hydroxy-3-methylpropyl)-4-phenylpiperidine;

4-(3-(3',5'-bis(trifluoromethyl)phenyl)-3-hydroxy-3-ethylpropyl)-4-phenylpiperidine;

4-(3-(3',5'-bis(trifluoromethyl)phenyl)propyl)-4-phenylpiperidine;

5-[4-(3-(3',5'-bis(trifluoromethyl)phenyl)propyl)-4-phenylpiperidin-1-ylmethyl]-2,4-dihydro-1,2,4-triazol-3-one;

5-[4-(3-(3',5'-bis(trifluoromethyl)phenyl)-3-hydroxypropyl) -4-phenylpiperidin-1-ylmethyl]-2,4-dihydro-1,2,4-triazol-3-one;

and pharmaceutically acceptable salts and prodrugs thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinomas such as small cell lung cancer; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg of a compound of formula (I) per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

Compounds of formula (I) wherein X represents C(=O)CH=CH or C(=O)CH=C($C_{1-6}$alkyl) may be prepared by reaction of compounds of formula (II) with compounds of formula (III):

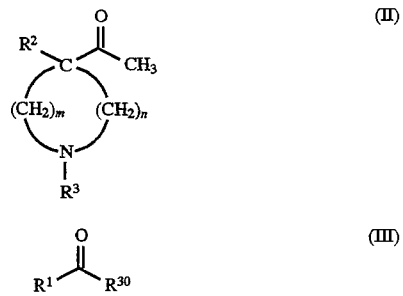

wherein $R^1$, $R^2$, $R^3$, m and n are as defined for formula (I) and $R^{30}$ represents H or $C_{1-6}$alkyl, in the presence of a base.

Suitable bases of use in the reaction include alkali metal alkoxides such as, for example, sodium methoxide.

The reaction is conveniently effected in a suitable organic solvent such as an alcohol, for example, methanol.

Compounds of formula (I) wherein X represents CH=CHC(=O) or C($C_{1-6}$alkyl)=CHC(=O) may be prepared by reaction of compounds of formula (IV) with compounds of formula (V):

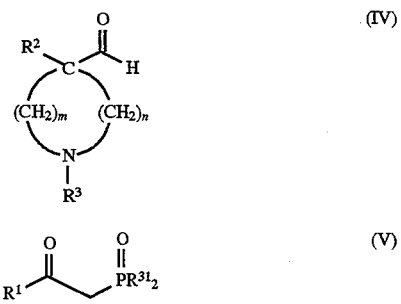

wherein $R^1$, $R^2$, $R^3$, m and n are as defined for formula (I) and $R^{31}$ represents alkoxy, in the presence of a base.

Suitable bases of use in the reaction include alkali metal carbonates such as, for example, potassium carbonate.

The reaction is conveniently carried out in a suitable organic solvent such as, for example, acetonitrile.

Other compounds of formula (I) may be prepared from compounds of formula (I) wherein X is C(=O)CH=CH, C(=O) CH=C($C_{1-6}$alkyl), CH=CHC(=O) and C($C_{1-6}$alkyl)=CHC(=O) by suitable interconversion procedures.

For example, compounds of formula (I) wherein X contains a carbon-carbon double bond may be converted to compounds of formula (I), wherein X contains no carbon-carbon double bond by reduction. Suitable procedures will be readily apparent to those skilled in the art and include catalytic hydrogenation, for example, using a nobel metal catalyst such as rhodium, platinum or, preferably, palladium, which may be supported, for example on carbon, and reaction with an alkyl tin hydride such as tributyl tin hydride.

Compounds of formula (I) wherein $R^4$ and $R^5$ together represent =O or $R^6$ and $R^7$ together represent =O may be converted to the corresponding alcohols wherein one of $R^4$ and $R^5$ or one of $R^6$ and $R^7$ is H and the other of $R^4$ and $R^5$ or $R^6$ and $R^7$ is hydroxy by conventional reduction methods. Suitable reducing agents include hydride reducing agents such as, for example, sodium borohydride.

Compounds of formula (I) wherein at least one of $R^4$, $R^5$, $R^6$ and $R^7$ represents $C_{1-6}$alkoxy may be prepared from the corresponding alcohol of formula (I) by alkylation. Suitable procedures will be readily apparent to those skilled in the art and include reaction with an alkyl halide, such as, for example, an alkyl iodide, in the presence of a base, such as an alkali metal hydride, for example sodium hydride.

Compounds of formula (I) wherein $R^4$ and $R^5$ or $R^6$ and $R^7$ together form =O may be converted to compounds of formula (I) wherein one or both of $R^4$ and $R^5$ or $R^6$ and $R^7$ represent $C_{1-6}$alkyl by reaction with a Grignard reagent of formula $R^4$MgHal and/or $R^5$MgHal or $R^6$MgHal and/or $R^7$MgHal wherein Hal represents halo such as chloro, bromo or iodo.

Compounds of formula (I) wherein X represents $CR^4R^5$CH=CH or CH=CH$CR^6R^7$ may be prepared from the corresponding compounds of formula (I) wherein X represents $CR^4R^5CH_2CHOH$ or $CH(OH)CH_2CR^6R^7$ by treatment with Burgess Reagent ((methoxycarbonylsulphamoyl)-triethylammonium hydroxide, inner salt).

Interconversion processes may also be used to vary the group $R^3$. For example, compounds of formula (I), (II) or (IV) wherein $R^3$ is other than H may be prepared from the corresponding compounds of formula (I), (II) or (IV) wherein $R^3$ is H by conventional methods, such as reaction with a compound $R^3$-Hal, where Hal represents halo, in the presence of a base. Suitable reagents and conditions will be readily apparent to those skilled in the art. Suitable bases include organic bases, such as tertiary amines, e.g. triethylamine, and inorganic bases, such as alkali metal carbonates, e.g. sodium carbonate. Compounds of formula (I), (II) or (IV) wherein $R^3$ is $COR^9$ may also be prepared from corresponding compounds of formula (I), (II) or (IV) wherein $R^3$ is H by, for example, reaction with an appropriate acid anhydride. Compounds of formula (I), (II) or (IV) wherein $R^3$ is $C_{1-6}$alkyl may be prepared from corresponding compounds of formula (I), (II) or (IV) wherein $R^3$ is $COR^9$ by reduction using, for example, borane or a borohydride such as sodium cyanoborohydride. Suitable procedures will be readily apparent to those skilled in the art. Compounds of formula (I), (II) or (IV) wherein $R^3$ is $C_{1-6}$alkyl substituted by $CONR^{10}R^{11}$ may be prepared from corresponding compounds of formula (I), (II) or (IV) wherein $R^3$ is $C_{1-6}$alkyl substituted by $CO_2R^{10}$ by treatment with ammonia or an amine of formula $NR^{10}R^{11}$.

Compounds of formula (II) wherein $R^3$ is H are commercially available or may be prepared by known procedures.

Compounds of formulae (III) and (V) are commercially available or may be prepared from commercially available compounds by procedures well known in the art.

Compounds of formula (IV) may be prepared from the corresponding compounds of formula (VI)

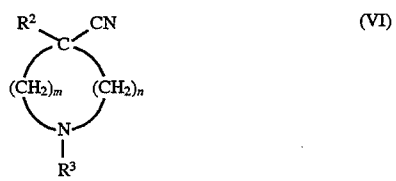

wherein $R^2$, $R^3$, m and n are as previously defined, by reduction.

A suitable reducing agent for use in the reaction is diisobutyl aluminium hydride.

Compounds of formula (VI) are commercially available or may be prepared by known procedures.

Where the above-described process for the preparation of the compounds according to the invention gives rise to mixtures of stereoisomers these isomers may, if desired, be separated, suitably by conventional techniques such as preparative chromatography.

The novel compounds which contain one or more chiral centres may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of the invention were tested by the methods set out at pages 36 to 39 of International Patent Specification No. WO 93/01165. The compounds were found to be active with $IC_{50}$ at the $NK_1$ receptor of less than 300 nM.

The compounds of this invention may be formulated as specifically illustrated at pages 35 to 36 of International Patent Specification No. 93/01165.

The following Examples illustrate the preparation of compounds according to the invention.

EXAMPLE 1

4-(3-(3',5'-Bis(trifluoromethyl)phenyl)propionyl)-4-phenylpiperidine Hydrochloride (a) 4-Acetyl-N-$^t$butoxycarbonyl-4-phenylpiperidine 4-Acetyl-4-phenylpiperidine hydrochloride was dissolved in water, the solution was made basic by addition of potassium carbonate, and the mixture was extracted with ethyl acetate. The extracts were dried ($Na_2SO_4$) and concentrated to give 4-acetyl-4-phenylpiperidine. To a solution of this compound (2.2 g) in dichloromethane (50 ml) was added di-$^t$butyl dicarbonate (2.8 g). After 15 minutes the solution was washed with water, dried, concentrated and the residue crystallised from petroleum ether to give the title compound, mp 91°–92° C.

(b) N-$^t$Butoxycarbonyl-4-(3',5'-bis(trifluoromethyl) cinnamoyl)-4-phenylpiperidine The compound of part (a) (9.3 g) in methanol (250 ml) was heated under reflux with 3,5-bis(trifluoromethyl) benzaldehyde (12.5 g) in the presence of sodium methoxide (0.5 g) for 3 hours. The solvent was removed in vacuo and the residue partitioned between water and ethyl acetate. The ethyl acetate solution was separated, dried and concentrated to give a residue which was purified by chromatography on silica gel eluting with ethyl acetate-petroleum ether (1:9) to give the title compound. $^1$H NMR (250 MHz, $CDCl_3$) δ1.45 (9H, s), 1.90–2.18 (2H, m), 2.40–2.50 (2H, m), 3.01–3.30 (2H, m), 3.70–4.10 (2H, m), 6.72 (1H, d, J=16 Hz), 7.26–7.44 (5H, m), 7.66 (1H, d, J=16 Hz), 7.79 (2H, s), 7.82 (1H, s).

(c) 4-(3-(3',5'-Bis(trifluoromethyl)phenyl)propionyl)-4-phenylpiperidine Hydrochloride The compound of part (b) (7.2 g) in toluene (50 ml) was purged with nitrogen gas and tributyltin hydride (4.8 g) was added. The reaction was heated to reflux for 16 hours then cooled and concentrated in vacuo. The product was purified by chromatography on silica eluting with ethyl acetate/petroleum ether (3:7), then dissolved in ethereal hydrogen chloride for 16 hours. The solvent was then evaporated to yield the title compound, mp 164°–165° C.; found: C, 56.82; H, 4.75; N, 2.95. $C_{22}H_{21}F_6NO·HCl$ requires C, 56.72; H, 4.76; N, 3.01.

EXAMPLE 2

4-(3-(3',5'-Bis(trifluoromethyl)phenyl)-1-hydroxy-3-propenyl)-4-phenylpiperidine Hydrochloride The compound of Example 1(b) (1 g) in methanol (20 ml) was stirred with sodium borohydride (0.2 g) for 1 hour. The solution was poured into water and extracted with ethyl acetate which was then dried ($Na_2SO_4$) and concentrated in vacuo. The residue was purified by chromatography on silica gel eluting with ethyl acetate-petroleum ether (3:7) then dissolved in ethereal hydrogen chloride. The solid which crystallised from solution was filtered to give the title compound, mp 174°–175° C.; found: C, 53.98; H, 4.76; N, 2.94. $C_{22}H_{21}F_6NO·HCl·1.25H_2O$ requires C, 54.10; H, 5.06; N, 2.89.

EXAMPLE 3

4-(3-(3',5'-Bis(trifluoromethyl)phenyl)-1-methoxy-3-propenyl)-4-phenylpiperidine Hydrochloride The compound of Example 1(b) was reduced with sodium borohydride as described in Example 2. After purification on silica gel the product was treated with sodium hydride and methyl iodide in dimethylformamide for one hour. The solution was poured onto water and extracted with ethyl acetate which was then dried ($Na_2SO_4$) and concentrated. The residue was purified by chromatography on silica gel eluting with ethyl acetate-petroleum ether (15:85), then dissolved in ethereal hydrogen chloride. The solid which crystallised from solution was filtered and dried to give the title compound, mp 282° C.; found: C, 57.06; H, 4.93; N, 2.88. $C_{23}H_{23}F_6NO.HCl.0.25H_2O$ requires C, 57.03;. H, 5.10; N, 2.89.

EXAMPLE 4

4-(3-(3',5'-Bis(trifluoromethyl)phenyl)-1-hydroxypropyl)-4-phenylpiperidine Hydrochloride The compound of Example 1(b) was treated with tributyltin hydride as described in Example 1(c). After purification on silica gel the product was reduced using sodium borohydride and treated with ethereal hydrogen chloride, as described in Example 2, to give the title compound, mp 90°–91° C.; found: C, 54.81; H, 5.04; N, 2.86. $C_{22}H_{23}F_6NO.HCl.0.75H_2O$ requires C, 54.89; H, 5.34; N, 2.91.

EXAMPLE 5

4-(3-(3',5'-Bis(trifluoromethyl)phenyl)-1-methoxypropyl)-4-phenylpiperidine Hydrochloride The compound of Example 1(b) was treated with tributyltin hydride then sodium borohydride as described in Example 4. After purification on silica gel the product was reacted with sodium hydride and methyl iodide by the method of Example 3. The product was purified on silica gel and dissolved in ethereal hydrogen chloride for 16 hours. The solvent was removed in vacuo to give the title compound, mp 65°–67° C.; found: C, 57.58; H, 5.36; N, 2.87. $C_{23}H_{25}F_6NO.HCl$ requires C, 57.32; H, 5.44; N, 2.91.

EXAMPLE 6

4-(3-(3',5'-Bis(trifluoromethyl)phenyl)-3-ketopropyl)-4-phenylpiperidine Hydrochloride (a) Dimethyl 2-(3,5-bis(trifluoromethyl)phenyl-2-ketoethylphosphonate Dimethyl methylphosphonate (50.1 g) in tetrahydrofuran (500 ml) was treated with butyl lithium (165 ml of a 2.5M solution in hexane) at −78° C. under an atmosphere of nitrogen. After 1 hour, methyl 3,5-bis(trifluoromethyl) benzoate (18.7 g) in tetrahydrofuran (50 ml) was added slowly and stirred for 0.5 hours. The reaction was quenched with 5N hydrochloric acid (500 ml) and the tetrahydrofuran evaporated in vacuo. The resulting mixture was extracted with ethyl acetate which was then dried and concentrated under reduced pressure. The residue was distilled under vacuum at 1 mm Hg to give the title compound, bp 160°–162° C.

(b) N-$^t$Butoxycarbonyl-4-phenyl-4-cyano piperidine

Di-$^t$butyldicarbonate (20 g) was added to a stirred solution of 4-phenyl-4-cyano piperidine hydrochloride (20 g) and Et$_3$N (9.5 g) in dry dichloromethane (100 ml). The resulting solution was stirred for 18 hours at room temperature. The reaction mixture was washed with water (100 ml) and the organic layer separated and dried over MgSO$_4$. Filtration and removal of solvent under reduced pressure afforded a white solid. Recrystallisation from hexane gave the title compound as white needles, mp=64° C. $^1$H NMR (360 MHz, CDCl$_3$) δ1.46 (9H, s), 1.90 (2H, m), 2.04 (2H, m), 3.20 (2H, m), 4.26 (2H, m), 7.26–7.49 (5H, m); MS (CI$^+$) 287 (M+H$^+$).

(c) N-$^t$Butoxycarbonyl-4-phenylpiperidine-4-carboxaldehyde

A solution of N-$^t$Butoxycarbonyl-4-phenyl-4-cyano piperidine (5.0 g) in dry toluene (100 ml) at −78° C. was treated with a solution of DIBALH (27.7 ml×1.0 mol) in toluene. The reaction was maintained at −78° C. for two hours, at which time it was quenched by slow addition of a saturated solution NH$_4$Cl (20 ml), and allowed to warm to room temperature. The reaction mixture was poured into water (100 ml) and extracted into ethyl acetate. The organic layers were separated, dried over MgSO$_4$, filtered and solvent removed to give a yellow oil. Chromatography on silica gel (20% EtOAc in hexane) afforded the product as a clear oil (2.1 g). $^1$NMR (360 MHz, CDCl$_3$) δ1.45 (9H, s), 1.95 (2H, m), 2.07 (2H, m), 3.12 (2H, m), 3.85 (2H, m), 7.26–7.40 (5H, m), 9.40 (1H, s); MS (CI$^+$) 290 (M+H$^+$).

(d) 4-(3-(3',5'-Bis(trifluoromethyl)phenyl)phenyl)-3-keto-2-propenyl)-4-phenyl-N$^t$butoxycarbonylpiperidine The compounds of Examples 6(a) (4.6 g) and 6(c) (5.8 g) were stirred in dimethylformamide (100 ml)in the presence of sodium hydride (0.8 g of a 60% dispersion in oil) for 1 hour. $^i$Propyl alcohol was added then the solvents were removed in vacuo. The residue was purified on silica gel eluting with ethyl acetate-petroleum ether (1:9) to give the title compound. $^1$H NMR (360 MHz, CDCl$_3$) δ1.46 (9H, s), 1.86–2.10 (2H, m), 2.30–2.46 (2H, m), 3.04–3.20 (2H, m), 3.84–3.98 (2H, m), 7.21–7.48 (5H, m), 7.99 (1H, s), 8.10 (2H, s).

(e) 4-(3-(3',5'-Bis(trifluoromethyl)phenyl)-3-ketopropyl)-4-phenyl-N$^t$butoxycarbonylpiperidine The compound of Example 6(c) (1.4 g) was shaken in ethanol (25 ml) under an atmosphere of hydrogen over 10% Pd-C (1 g) at 50 psi for 16 hours. The mixture was filtered and evaporated to give the title compound. $^1$H NMR (360 MHz, CDCl$_3$) δ1.45 (9H, s), 2.04–2.14 (2H, m), 2.25–2.35 (2H, m), 3.42–3.49 (2H, m), 3.55–3.62 (2H, m), 6.61 (1H, d, J=16 Hz), 7.15 (1H, d, J=16 Hz), 7.26–7.46 (5H, m), 8.03 (1H, s), 8.22 (2H, s).

(f) 4-(3-(3',5'-Bis(trifluoromethyl)phenyl)-3-ketopropyl)-4-phenylpiperidine Hydrochloride The compound of Example 6(d) was treated with ethereal hydrogen chloride for 16 hours then concentrated in vacuo to give the title compound as a white solid, mp 54°–55° C.; found: C, 55.48; H, 4.74; N, 2.78. $C_{22}H_{21}F_6NO.HCl.0.5H_2O$ requires C, 55.64; H, 4.88; N, 2.95.

EXAMPLE 7

4-(3-(3',5'-Bis(trifluoromethyl)phenyl)-3-hydroxypropyl)-4-phenylpiperidine Hydrochloride (a) 4-(3-(3',5'-Bis(trifluoromethyl)phenyl)-3-hydroxypropyl)-N-$^t$butoxycarbonyl-4-phenylpiperidine The compound of Example 6(e) (1.5 g) in methanol (20 ml) was treated with sodium borohydride (0.3 g) for 1 hour. The reaction mixture was poured onto water and extracted with ethyl acetate which was then dried ($Na_2SO_4$) and concentrated. The residue was purified by chromatography on silica gel eluting with ethyl acetate-petroleum ether (1:4) to give the title compound. $^1$H NMR (360 MHz, CDCl$_3$) δ1.43 (9H, s), 1.47–1.73 (2H, m), 2.04–2.17 (2H, m), 3.02–3.14 (2H, m), 3.58–3.66 (2H, m), 4.56–4.58 (1H, m), 7.19–7.34 (5H, m), 7.61 (2H, s), 7.74 (1H, s).

(b) 4-(3-(3',5'-Bis(trifluoromethyl)phenyl)-3-hydroxypropyl)-4-phenylpiperidine Hydrochloride The compound of part (a) was dissolved in ethereal hydrogen chloride for 16 hours. The solvent was evaporated in vacuo to give the title compound, mp 95°–96° C.

EXAMPLE 8

4-(3-(3',5'-Bis(trifluoromethyl)phenyl)-3-methoxypropyl)-4-phenylpiperidine Hydrochloride The compound of Example 7(a) (0.5 g) in dimethylformamide (20 ml) was stirred with methyl iodide (0.29 g) and sodium hydride (0.06 g of a 60% suspension in oil) for 16 hours. The reaction mixture was diluted with ethyl acetate, washed with water, dried (Na$_2$SO$_4$) and concentrated. The residue was purified by chromatography on silica gel then dissolved in ethereal hydrogen chloride for 16 hours. The solvent was removed under reduced pressure to give the title compound as a white solid, mp 186°–187° C.; found: C, 55.27; H, 5.47; N, 2.82. C$_{23}$H$_{25}$F$_6$NO.HCl.H$_2$O requires C, 55.26; H, 5.65; N, 2.80.

EXAMPLE 9

R- and S-4-(3-(3', 5'-Bis(trifluoromethyl)phenyl-3-hydroxypropyl)-4-phenylpiperidine Hydrochloride The compound of Example 7(a) (100 mg) was dissolved in dichloromethane (10 ml) and stirred for 1.5 hours with triethylamine (0.03 ml), 4-(dimethylamino)pyridine (5 mg) and α-methoxyl-α-(trifluoromethyl)phenylacetyl chloride (0.04 ml). The solvent was removed under reduced pressure and the residue partitioned between ethyl acetate and water. The ethyl acetate solution was concentrated and the residue purified by chromatography on silica gel eluting with ethyl acetate-petroleum ether (7:93) to give two products, diastereomer A and diastereomer B. These two diastereomers were individually heated under reflux with sodium hydroxide in methanol for 1 hour. In each case the solvent was removed in vacuo and the residue purified by chromatography on silica gel eluting with ethyl acetate-petroleum ether (1:4) to give R- and S-4-(3-(3',5'-bis(trifluoromethyl)phenyl)-3-hydroxypropyl)-N-$^t$butoxycarbonyl-4-phenylpiperidine. These two enantiomers were individually treated with ethereal hydrogen chloride as described in Example 7(b) to give the title compounds. Enantiomer A, mp 81°–82° C., α$_D$ (c=1.03, MeOH)=+9.32°; Enantiomer B, mp 83°–84° C., α$_D$ (c=0.96, MeOH)=−8.85°.

EXAMPLE 10

4-(3-(3', 5'-Bis(trifluoromethyl)phenyl)-3-hydroxy-3-methylpropyl)-4-phenylpiperidine Hydrochloride The compound of Example 6(c) (0.41 g) in diethyl ether (10 ml) was treated with methylmagnesium bromide (0.8 ml of a 3M solution in tetrahydrofuran) for 5 minutes after which time water was added and extracted with diethyl ether. The ethereal extracts were dried (Na$_2$SO$_4$) and concentrated to give a residue which was purified by chromatography on silica gel eluting with ethyl acetate-petroleum ether (1:3). The resulting oil was treated with ethereal hydrogen chloride for 4 hours then concentrated to give the title compound as a white solid, mp 213–215° C.; found: C, 56.26; H, 5.42; N, 2.93. C$_{23}$H$_{25}$F$_6$NO.HCl. 0.5H$_2$O requires C, 56.27; H, 5.54; N, 2.85.

EXAMPLE 11

4-(3-(3',5'-Bis(trifluoromethyl)phenyl)-3-hydroxy-3-ethylpropyl)-4-phenylpiperidine Hydrochloride Prepared by the method of Example 10 using ethylmagnesium bromide. Mp 105° C.; found: C, 57.13; H, 5.83; N, 2.76. C$_{24}$H$_{27}$F$_6$NO.HCl0.5H$_2$O requires C, 57.09; H, 5.79; N, 2.77.

EXAMPLE 12

4-(3-(3',5'-Bis(trifluoromethyl)phenyl)propyl)-4-phenylpiperidine Hydrochloride

The compound of Example 7(a) (0.7 g) in dichloromethane (50 ml) with 4-(dimethylamino)pyridine (0.32 g) was cooled to 0° C. Phenyl chlorothiocarbamate (0.43 g) was added and the solution allowed to warm to 20° C. and stirred for 16 hours. The mixture was diluted with ethyl acetate and washed successively with a solution of citric acid in water, then water, sodium bicarbonate solution, and water. The solution was dried (Na$_2$SO$_4$), concentrated and the residue purified by chromatography on silica gel eluting with ethyl acetate-petroleum ether (1:9). The resulting product was dissolved in toluene (25 ml) which was purged with nitrogen gas. Alpha, alpha'-azoisobutyronitrile (0.49 g) and tributyltin hydride (0.58 g) were added and the solution was heated under reflux for 5 hours then cooled and concentrated under reduced pressure. The residue was purified by chromatography on silica gel eluting with ethyl acetate-petroleum ether (1:9) then treated with ethereal hydrogen chloride for 16 hours. The solvent was removed in vacuo and the residue crystallised from ethyl acetate to give the title compound. $^1$H NMR (360 MHz, D$_6$-DMSO) δ1.22–1.32 (2H, m), 1.54–1.64 (2H, m), 1.83–1.94 (2H, m), 2.26–2.34 (2H, m), 2.62 (2H, t, J=7.5 Hz), 2.72 (2H, t, J=10 Hz), 3.08–3.18 (2H, m), 7.21–7.37 (5H, m), 7.76 (2H, s), 7.86 (1H, s), 8.74 (1H, s); MS (CI$^+$) 416 (M+H)$^+$.

EXAMPLE 18

5-[4-(3-(3',5'-Bis(trifluoromethyl)phenyl)propyl)-4-phenylpiperidin-1-ylmethyl]-2,4-dihydro-1,2,4-triazol-3-one N-$^t$-Butoxychloromethyl imidrazone (104.4 mg) was added to a stirred suspension of the compound of Example 12 (310 mg) and K$_2$CO$_3$ (1.0 g) in dry dimethylformamide (15 ml). The resulting mixture was stirred at room temperature for 18 hours. The reaction mixture was then diluted with water (50 ml) and extracted into ethyl acetate (50 ml). The organic extract was washed with water (4×20 ml), brine (50 ml) and dried over MgSO$_4$. Filtration and removal of solvent under reduced pressure afforded a yellow crystalline solid (290 mg) which was re-dissolved in dry toluene (20 ml) and warmed to reflux in the presence of a catalytic amount of potassium t-butoxide. After 4 hours the reaction was cooled to room temperature and the solvent removed Under reduced pressure. Recrystallisation from diethyl ether-hexane afforded the title compound as a white powder, mp 104°–105° C.

EXAMPLE 14

5-[4-(3-(3',5'-Bis(trifluoromethyl)phenyl)-3-hydroxypropyl)-4-phenylpiperidin-1-ylmethyl]-2,4-dihydro-1,2,4-triazol-3-one Prepared from the compound of Example 7 using the method of Example 7 using the method of Example 14. Mp 110° C.; found: C, 55.30; H, 5.05; N, 10.09. $C_{25}H_{26}F_6N_4O_2 \cdot 0.75H_2O$ requires C, 55.40; H, 5.11; N, 10.33.

We claim:

1. A compound of formula (I), or a pharmaceutically acceptable salt thereof:

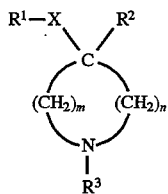

wherein

X represents a propylene or propenylene chain optionally substituted by one or more of $R^4$, $R^5$, $R^6$ and $R^7$;

m is 2, 3 or 4;

n is 0, 1 or 2 when m is 2 or 3, and n is 0 or 1 when m is 4;

$R^1$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONHphenyl(C_{1-4}alkyl)$, $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), Y—$R^8$ or CO—Z—$(CH_2)_q$—$R^{12}$;

$R^4$ and $R^5$ each independently represents H, $C_{1-6}$alkyl, $C_{3-6}$cycloalkyl, $C_{3-5}$cycloalkylmethyl, hydroxy or $C_{1-6}$alkoxy, or $R^4$ and $R^5$ together form a group =O;

$R^6$ and $R^7$ each independently represents H, $C_{1-6}$alkyl, $C_{3-6}$cycloalkyl, $C_{3-5}$cycloalkylmethyl, hydroxy or $C_{1-6}$alkoxy or $R^6$ and $R^7$ together form a group =O;

$R^8$ represents an optionally substituted aromatic heterocycle;

$R^9$ represents H, $C_{1-6}$alkyl, $C_{3-6}$cycloalkyl, $C_{3-5}$cycloalkylmethyl, or phenyl;

$R^{10}$ and $R^{11}$ each independently represent H, $C_{1-6}$alkyl, $C_{3-6}$cycloalkyl or $C_{3-5}$cycloalkylmethyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, $C_{3-6}$cycloalkyl, $C_{3-5}$cycloalkylmethyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl; $R^{15}$ represents $C_{1-6}$alkyl, $C_{3-6}$cycloalkyl, $C_{3-5}$cycloalkylmethyl, trifluoromethyl or phenyl optionally substituted by one or more substituents selected from $C_{1-6}$alkyl, $C_{1-6}$alkoxy, halo and trifluoromethyl;

Y represents a hydrocarbon chain of 1, 2, 3 or 4 carbon atoms which may optionally be substituted by oxo;

Z represents $CH_2$, O, S or $NR^{10}$; and q represents 0, 1, 2, 3, 4, 5 or 6.

2. A compound of formula (I), or a pharmaceutically acceptable salt thereof:

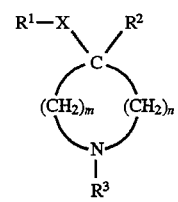

wherein

X represents a group $CR^4R^5CH_2CR^6R^7$, $CR^4$=$CHCR^6R^7$ or $CR^4R^5CH$=$CR^6$;

m is 2, 3 or 4;

n is 0, 1 or 2 when m is 2 or 3, and n is 0 or 1 when m is 4;

$R^1$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONHphenyl(C_{1-4}alkyl)$, $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy; halo and trifluoromethyl), Y—$R^8$ or CO—Z—$(CH_2)_q$—$R^{12}$;

$R^4$ and $R^5$ each independently represents H, $C_{1-6}$alkyl, $C_{3-6}$cycloalkyl, $C_{3-5}$cycloalkylmethyl, hydroxy or $C_{1-6}$alkoxy, or $R^4$ and $R^5$ together form a group =O;

$R^6$ and $R^7$ each independently represents H, $C_{1-6}$alkyl, $C_{3-6}$cycloalkyl, $C_{3-5}$cycloalkylmethyl, hydroxy or $C_{1-6}$alkoxy or $R^6$ and $R^7$ together form a group =O;

$R^8$ represents an optionally substituted aromatic heterocycle;

$R^9$ represents H, $C_{1-6}$alkyl, $C_{3-6}$cycloalkyl, $C_{3-5}$cycloalkylmethyl, or phenyl;

$R^{10}$ and $R^{11}$ each independently represent H, $C_{1-6}$alkyl, $C_{3-6}$cycloalkyl or $C_{3-5}$cycloalkylmethyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, $C_{3-6}$cycloalkyl, $C_{3-5}$cycloalkylmethyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, $C_{3-6}$cycloalkyl, $C_{3-5}$cycloalkylmethyl, trifluoromethyl or phenyl optionally substituted by one or more substituents selected from $C_{1-6}$alkyl, $C_{1-6}$alkoxy, halo and trifluoromethyl;

Y represents a hydrocarbon chain of 1, 2, 3 or 4 carbon atoms which may optionally be substituted by oxo;

Z represents $CH_2$, O, S or $NR^{10}$; and q represents 0, 1, 2, 3, 4, 5 or 6.

3. A compound of formula (I), or a pharmaceutically acceptable salt thereof:

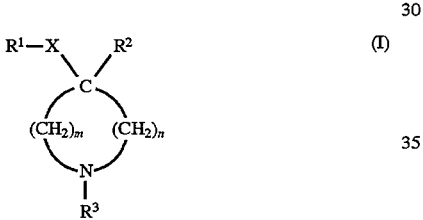

wherein

X represents a group $CR^4R^5CH_2CR^6R^7$, $CR^4$=$CHCR^6R^7$ or $CR^4R^5CH$=$CR^6$;

m is 2, 3 or 4;

n is 0, 1 or 2 when m is 2 or 3, and n is 0 or 1 when m is 4;

$R^1$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ each independently represent H, $C_{1-6}$alkyl, phenyl or trifluoromethyl;

$R^2$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$CO_2R^a$ or —$CONR^aR^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl;

$R^3$ represents H, $COR^9$, $CO_2R^{10}$, $COCONR^{10}R^{11}$, $COCO_2R^{10}$, $SO_2R^{15}$, $CONR^{10}SO_2R^{15}$, $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONH$phenyl($C_{1-4}$alkyl), $COCO_2R^{10}$, $COCONR^{10}R^{11}$, $SO_2R^{15}$, $CONR^{10}SO_2R^{15}$ and phenyl optionally substituted by one or more substituents selected from $C_{1-6}$alkyl, $C_{1-6}$alkoxy, halo and trifluoromethyl), Y—$R^8$ or CO—Z—$(CH_2)_q$—$R^{12}$;

$R^4$ and $R^5$ each independently represents H, $C_{1-6}$alkyl, hydroxy or $C_{1-6}$alkoxy, or $R^4$ and $R^5$ together form a group =O;

$R^6$ and $R^7$ each independently represents H, $C_{1-6}$alkyl, hydroxy or $C_{1-6}$alkoxy or $R^6$ and $R^7$ together form a group =O;

$R^8$ represents an optionally substituted aromatic heterocycle;

$R^9$ represents H, $C_{1-6}$alkyl or phenyl;

$R^{10}$ and $R^{11}$ each independently represent H or $C_{1-6}$alkyl;

$R^{12}$ represents $NR^{13}R^{14}$ or an optionally substituted aromatic or non-aromatic azacyclic or azabicyclic group;

$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

$R^{15}$ represents $C_{1-6}$alkyl, trifluoromethyl or phenyl optionally substituted by one or more substituents selected from $C_{1-6}$alkyl, $C_{1-6}$alkoxy, halo and trifluoromethyl;

Y represents a hydrocarbon chain of 1, 2, 3 or 4 carbon atoms which may optionally be substituted by oxo;

Z represents $CH_2$, O, S or $NR^{10}$; and q represents 0, 1, 2, 3, 4, 5 or 6.

4. A compound as claimed in claim 1 of formula (Ia), or a pharmaceutically acceptable salt thereof:

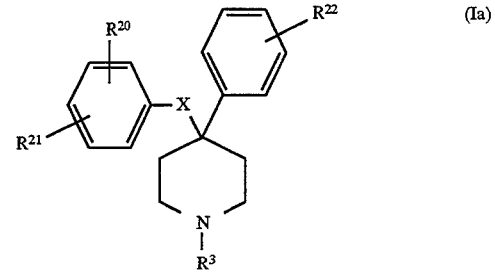

wherein $R^3$ and X are as claimed in claim 1;

$R^{20}$ and $R^{21}$ independently represent H, $C_{1-6}$alkyl, $C_{2-6}$alkenyl, $C_{2-6}$alkynyl, $C_{3-6}$cycloalkyl, $C_{3-5}$cycloalkylmethyl, halo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $CO_2R^a$, or $CONR^aR^b$, where $R^a$ and $R^b$ are as previously defined; and $R^{22}$ represents H or halo.

5. A compound as claimed in claim 1 wherein m is 2 and n is 2.

6. A compound as claimed in claim 1 wherein $R^4$, $R^5$, $R^6$ and $R^7$ each independently represent H, methyl, hydroxy or methoxy or $R^4$ and $R^5$, or $R^6$ and $R^7$, together represent =O.

7. A compound as claimed in claim 1 wherein X represents a group selected from:

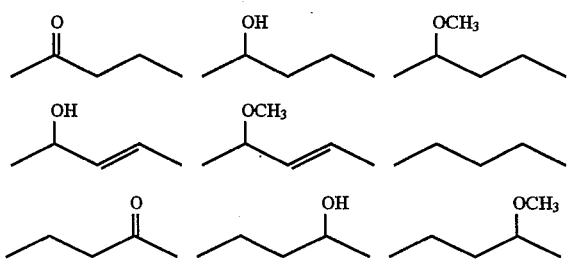

8. A compound as claimed in claim 7 wherein X represents $CH_2CH_2CH(OH)$.

9. A compound as claimed in claim 1 wherein $R^1$ represents phenyl substituted by 1, 2 or 3 groups selected from nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy.

10. A compound as claimed in claim 9 wherein $R^1$ represents 3,5-disubstituted phenyl wherein the substituents are selected from $C_{1-6}$alkyl, halo and trifluoromethyl.

11. A compound as claimed in claim 10 wherein $R^1$ represents 3,5-bis(trifluoromethyl)phenyl.

12. A compound as claimed in claim 1 wherein $R^2$ represents unsubstituted or substituted phenyl.

13. A compound as claimed in claim 1 wherein $R^3$ is H.

14. A compound as claimed in claim 1 wherein $R^3$ is Y—$R^8$ wherein Y is as defined in claim 1 and $R^8$ is selected from thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted by one or more of $C_{1-6}$alkyl, $C_{3-6}$cycloalkyl, $C_{3-5}$cycloalkylmethyl, $C_{1-6}$alkoxy, phenyl, oxo, thioxo, halo, trifluoromethyl, $NR^aR^b$, $NR^aCOR^b$, $CONR^aR^b$, $CO_2R^a$, $SR^a$, $SO_2R^a$ and $CH_2OR^a$, where $R^a$ and $R^b$ are as defined in claim 1.

15. A compound as claimed claim 1 wherein Y represents a hydrocarbon chain of 1 or 2 carbon atoms optionally substituted by oxo.

16. A compound selected from
4-(3-(3',5'-bis(trifluoromethyl)phenyl)propionyl)-4-phenylpiperidine;
4-(3-(3',5'-bis(trifluoromethyl)phenyl)-1-hydroxy-3-propenyl)-4-phenylpiperidine;
4-(3-(3',5'-bis(trifluoromethyl)phenyl)-1-methoxy-3-propenyl)-4-phenylpiperidine;
4-(3-(3',5'-bis(trifluoromethyl)phenyl)-1-methoxypropyl)-4-phenylpiperidine;
4-(3-(3',5'-bis(trifluoromethyl)phenyl)-1-hydroxypropyl)-4-phenylpiperidine;
4-(3-(3',5'-bis(trifluoromethyl)phenyl)-3-ketopropyl)-4-phenylpiperidine;
4-(3-(3',5'-bis(trifluoromethyl)phenyl)-3-hydroxypropyl)-4-phenylpiperidine;
4-(3-(3',5'-bis(trifluoromethyl)phenyl)-3-methoxypropyl)-4-phenylpiperidine;
(R)-4-(3-(3',5'-bis(trifluoromethyl)phenyl)-3-hydroxypropyl)-4-phenylpiperidine;
(S)-4-(3-(3',5'-bis(trifluoromethyl)phenyl)-3-hydroxypropyl)-4-phenylpiperidine;
4-(3-(3',5'-bis(trifluoromethyl)phenyl)-3-hydroxy-3-methylpropyl)-4-phenylpiperidine;
4-(3-(3',5'-bis(trifluoromethyl)phenyl)-3-hydroxy-3-ethylpropyl)-4-phenylpiperidine;
4-(3-(3',5'-bis(trifluoromethyl)phenyl)propyl)-4-phenylpiperidine;
5-[4-(3-(3',5'-bis(trifluoromethyl)phenyl)propyl)-4-phenylpiperidin-1-ylmethyl]-2,4-dihydro-1,2,4-triazol-3-one;
5-[4-(3-(3',5'-bis(trifluoromethyl)phenyl)-3-hydroxypropyl)-4-phenylpiperidin-1-ylmethyl]-2,4-dihydro-1,2,4-triazol-3-one;
or a pharmaceutically acceptable salt thereof.

17. A pharmaceutical composition comprising a compound as claimed in claim 1 or a pharmaceutically acceptable salt thereof in association with a pharmaceutically acceptable carrier.

18. A process for the preparation of a compound as claimed in claim 1 or a pharmaceutically acceptable salt thereof which comprises:

(A) reacting a compound of formula (II) with a compound of formula (III)

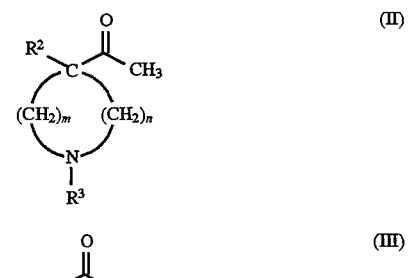

wherein $R^1$, $R^2$, $R^3$, m and n are as defined in claim 1 and $R^{30}$ represents H or $C_{1-6}$alkyl, in the presence of a base; or (B) reacting a compound of formula (IV) with a compound of formula (V)

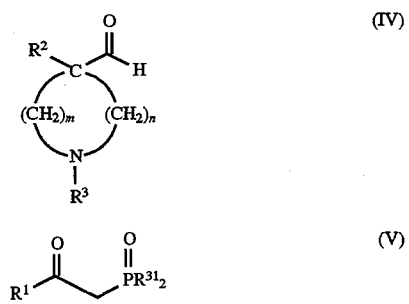

wherein $R^1$, $R^2$, $R^3$, m and n are as defined in claim 1 and $R^{31}$ represents $C_{1-6}$alkoxy, in the presence of a base;

in each case followed, if desired, by interconversion into another compound of formula (I) or (Ia); and/or followed, if necessary, by deprotection.

19. A method for the treatment of a condition selected from the group consisting of pain, inflammation, migraine, emesis and postherpetic neuralgia, which method comprises the administration to a patient in need thereof of an effective amount of the compound of claim 1, or a pharmaceutically acceptable salt thereof.

* * * * *